US00PP34648P2

(12) United States Plant Patent
Schmidt

(10) Patent No.: US PP34,648 P2
(45) Date of Patent: Oct. 11, 2022

(54) ***FESTUCA* PLANT NAMED 'GLOW STICKS'**

(50) Latin Name: *Festuca arundinacea*
Varietal Denomination: 'Glow Sticks'

(71) Applicant: Jeremy Schmidt, Raleigh, NC (US)

(72) Inventor: Jeremy Schmidt, Raleigh, NC (US)

( * ) Notice: Subject to any disclaimer, the term of this patent is extended or adjusted under 35 U.S.C. 154(b) by 0 days.

(21) Appl. No.: 17/351,166

(22) Filed: Jun. 17, 2021

(51) Int. Cl.
*A01H 5/12* (2018.01)
*A01H 6/46* (2018.01)

(52) U.S. Cl.
USPC ..... Plt./384
CPC ..... *A01H 6/4618* (2018.05)

(58) Field of Classification Search
USPC ..... Plt./384
CPC ..... A01H 6/4618; A01H 5/12
See application file for complete search history.

*Primary Examiner* — Keith O. Robinson
(74) *Attorney, Agent, or Firm* — Penny J. Aguirre

(57) ABSTRACT

A new cultivar of *Festuca* plant named 'Glow Sticks' that is characterized by its light yellow flower stalks and inflorescences that rise above a dark green tuft of foliage and its foliage that is dark green in color with a subtle central stripe that is white in color.

1 Drawing Sheet

Botanical classification: *Festuca arundinacea.*
Varietal denomination: 'Glow Sticks'.

BACKGROUND OF THE INVENTION

The present invention relates to a new and distinct cultivar of *Festuca arundinacea* and will be referred to hereafter by its cultivar name, 'Glow Sticks'. 'Glow Sticks' is a new cultivar of perennial ornamental grass grown for container and landscape use.

The new cultivar, 'Glow Sticks' was discovered by the Inventor as a chance seedling in May 2014 that was growing in a garden in Wake Co, N.C. The exact parentage is unknown; however, it is most likely a seedling of an unnamed plant of *Festuca arundinacea* based on its characteristics and its proximity to the new cultivar. The new cultivar underwent several division selections until a stable central stripe on the leaf was obtained in October 2016.

Asexual propagation of the new cultivar was first accomplished by division by the Inventor in Raleigh, N.C. in 2017. Asexual propagation by division has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Glow Sticks' as a unique cultivar of *Festuca.*

1. 'Glow Sticks' exhibits light yellow flower stalks and inflorescences that rise above a dark green tuft of foliage.
2. 'Glow Sticks' exhibits foliage that is dark green in color with a subtle central stripe that is white in color.

Typical plants of *Festuca arundinacea* differs from 'Glow Sticks' in having foliage that is all green in color and flower stalks and inflorescences that are all green in color. Although a few agronomic varieties have been named based on adapting to certain agronomic growing conditions, there are no known cultivars of *Festuca arundinacea* with unique ornamental characteristics known to the Inventor. 'Glow Sticks' can be compared to *Bromus inermis* cultivar 'Skinner's Gold' (not patented). 'Skinner's Gold' is similar to 'Glow Sticks' in having yellow inflorescences and leaves with a white central stripe. In addition to being a different genus, 'Skinner's Gold' differs from 'Glow Sticks' in having leaves with a much wider white central stipe.

BRIEF DESCRIPTION OF THE DRAWING

The accompanying color photograph illustrates the overall appearance and distinct characteristics of the new *Festuca*. The photograph was taken of a group of 24-month-old plants (from 4-inch wide divisions) of 'Glow Sticks' as grown outdoors in a garden in Raleigh, N.C. The photograph illustrates the overall plant habit and appearance of 'Glow Sticks' in bloom. The colors in the photograph are as close as possible with the photographic and printing technology utilized and the color values cited in the detailed botanical description accurately describe the colors of the new *Festuca.*

DETAILED BOTANICAL DESCRIPTION

The following is a detailed description of 6-month-old plants (from a 6-inch wide division) of ' Glow Sticks' as grown outdoors in one-gallon containers in Raleigh, N.C. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—May to July in North Carolina.

*Plant type.*—Evergreen to semi-evergreen perennial grass.

*Plant growth habit*.—Tight mound of stiff foliage, erect to semi-erect foliage with upright flowering stalks held above the foliage.

*Height and spread*.—Average of 48 cm in height and 34 cm in diameter as a 23-month-old plant in a one-gallon container, reaches an average of 90 cm in height and 50 cm in width, (foliage an average of 50 cm in height) as a 5 year-old plant in the landscape.

*Hardiness*.—At least in U.S.D.A. Zones 3 to 9.

*Diseases and pests*.—No susceptibility or resistance to pests and diseases has been observed.

*Root description*.—Fibrous and fine, 162A in color.

*Propagation*.—Division.

*Time required for root initiation*.—An average of 1 to 2 weeks for root initiation, an average of 4 to 6 weeks to produce a young plant from a rooted cutting.

*Growth rate*.—Moderate in the garden and vigorous in a nursery container.

*Branching*.—Main shoots grow from the base, no lateral branches.

Foliage description:

*Leaf shape*.—Linear.

*Leaf division*.—Simple.

*Leaf base*.—Sheathed.

*Leaf apex*.—Long and narrowly acuminate.

*Leaf aspect*.—Carinate, upright and outward.

*Leaf venation*.—Parallel, upper and lower surface color; veins inconspicuous, except the main center vein; 157A in color.

*Leaf margins*.—Entire.

*Leaf size*.—Average of 31 cm in length, 5 mm in width.

*Leaf number*.—Average of 3 leaves per shoot.

*Leaf arrangement*.—Tufted, alternate growing in basal leafy shoots.

*Leaf surface*.—Both surfaces glabrous, matte and smooth.

*Sheath*.—Long and narrowly acuminate in aspect, average of 1.5 cm in length, 1.5 mm in width, color a blend of 139A and 144A, base 145D.

*Leaf color*.—Young leaves upper and lower surface; 144A, mature leaves upper and lower surface; 139A, dried leaves; 161C.

Flower description:

*General description*.—Compact, numerous slender, silky aggregate racemes, cascading, spikelets arranged in pairs.

*Lastingness of inflorescence*.—Average of 1 month, persistent.

*Fragrance*.—None.

*Panicle size*.—An average of 23 cm in length and 7 cm in width.

*Flower number*.—Average of 200 flowers per raceme, average of 2,000 flowers per flowering stem.

*Flower buds*.—An average of 1 cm in length, 2 mm in diameter, narrow and linear in shape, color; a blend of 143A, 145C, slightly tinged 8A in center and base, surface is smooth, glabrous, glossy.

*Flowers*.—Single, consisting of two glumes, one palea and one lemma, upright aspect, freely flowering habit, average of 1 mm in length, 2 mm in width.

*Peduncle*.—An average of 30 cm in length and 2 mm in width, moderately strong, smooth and glabrous, matte and color; young 9C in color, mature 9A in color.

*Rachis*.—An average of 5 cm in length and 2 mm in width, moderately strong, smooth and glabrous, matte, color; young 9C in color, mature 9A in color.

*Pedicels*.—An average of 6 mm in length and 0.4 mm in width, moderately strong, smooth and glabrous, matte, color; young 9C in color, mature 10A in color.

*Spikelet description*.—Consisting of 2 glumes, 1 palea, 1 lemma, surface glossy, ovate in shape, strongly concave, base cuneate, no venation visible, not fading, 2 glumes oppositely placed at the base of each individual flower, lemma and palea oppositely placed above the glumes, margins of glumes and lemma entire, margins of palea fringed, apex of glumes and palea acute, apex of lemma narrow acute, average length of lower glume 4 mm, upper glume 6 mm in length, length of lemma 8 mm, length of palea 4 mm, glume and palea width 0.75 mm, width of lemma 0.5 mm, color; both surfaces of glumes 164C, lemma and palea N155A, tip of lemma 165B.

Reproductive organs:

*Androecium*.—Stamens; average of 3, anthers; narrow oblong in shape, 2 mm in length, 0.3 mm in width, 18A in color, filament; average of 0.5 mm in length, NN155C in color, pollen; none.

*Gynoecium*.—Pistil; 2, 3 mm in length, stigmas; feather-like, 0.3 mm in length, en masse; 1 mm in diameter, NN155C in color, style; 1 mm in length, NN155D in color, ovary; minute and 144A in color.

*Caryopsis*.—No caryopsis production was observed.

It is claimed:

1. A new and distinct cultivar of *Festuca* plant named 'Glow Sticks' as herein illustrated and described.

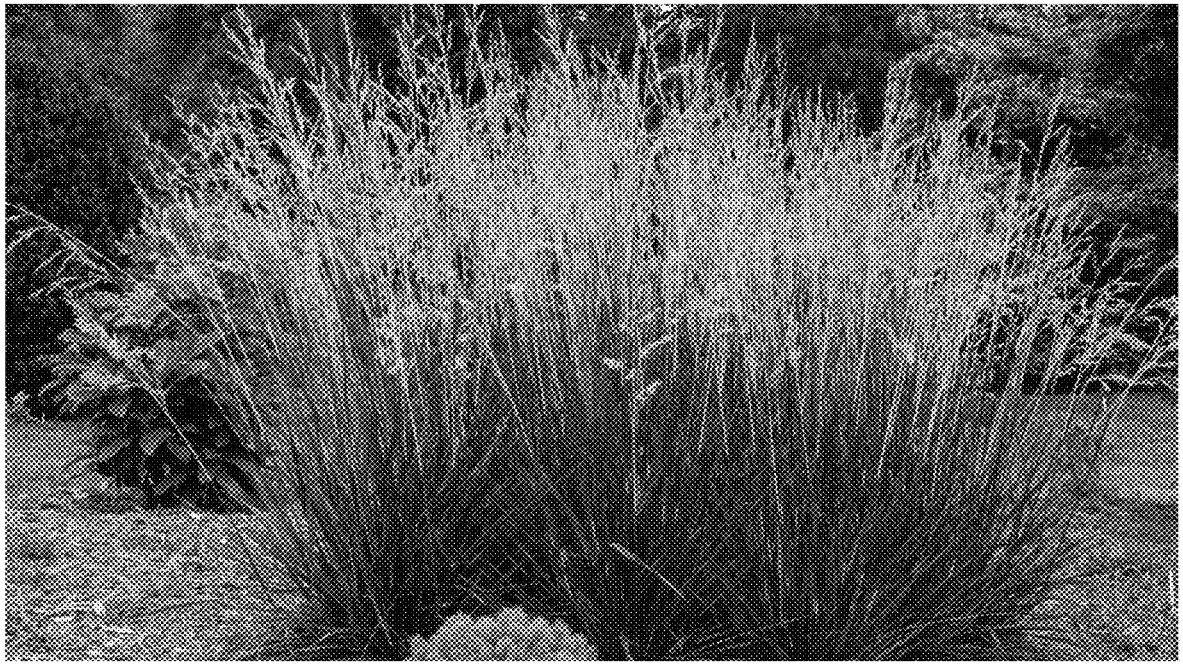

* * * * *